United States Patent [19]

Patel

[11] Patent Number: 5,738,678
[45] Date of Patent: Apr. 14, 1998

[54] APPARATUS AND METHOD FOR DELIVERING LASER RADIATION TO A SUBSTRATE

[75] Inventor: Bipin Chandra Muljibhai Patel, Greenford, United Kingdom

[73] Assignee: British Technology Group Limited, London, England

[21] Appl. No.: 532,719

[22] PCT Filed: May 6, 1994

[86] PCT No.: PCT/GB94/00976

§ 371 Date: Oct. 12, 1995

§ 102(e) Date: Oct. 12, 1995

[87] PCT Pub. No.: WO94/26203

PCT Pub. Date: Nov. 24, 1994

[30] Foreign Application Priority Data

May 7, 1993 [GB] United Kingdom ............ 9309397

[51] Int. Cl.⁶ .................................................. A61H 5/06
[52] U.S. Cl. .............................. 606/10; 606/3; 606/13; 433/29; 433/215
[58] Field of Search .................. 606/2–19; 433/29–31, 433/215

[56] References Cited

U.S. PATENT DOCUMENTS

| | | |
|---|---|---|
| 4,445,858 | 5/1984 | Johnson . |
| 4,503,853 | 3/1985 | Ota . |
| 4,560,351 | 12/1985 | Osborne .......................... 433/215 |
| 4,611,992 | 9/1986 | Lokken ............................. 433/29 |
| 4,648,892 | 3/1987 | Kittrell . |
| 4,736,745 | 4/1988 | Gluckman . |
| 5,007,837 | 4/1991 | Werly ............................... 433/29 |
| 5,090,908 | 2/1992 | Teumim-Stone . |
| 5,171,150 | 12/1992 | Levy . |
| 5,194,005 | 3/1993 | Levy . |
| 5,199,870 | 4/1993 | Steiner et al. .................... 433/29 |

FOREIGN PATENT DOCUMENTS

| | | |
|---|---|---|
| 0 184 928 | 6/1986 | European Pat. Off. . |
| 0 438 353 A1 | 7/1991 | European Pat. Off. . |
| 2 599 961 | 12/1987 | France . |
| 323007 A1 | 3/1983 | Germany . |
| 85/00010A1 | 10/1985 | WIPO . |

*Primary Examiner*—David M. Shay
*Attorney, Agent, or Firm*—Nixon & Vanderhye

[57] ABSTRACT

The invention provides an apparatus and method for delivering laser radiation to a substrate (20,120) involving a laser radiation source (1), delivery means (2) to transmit the laser radiation from the source, a delivery head (3) to direct the laser radiation from the delivery means onto the substrate. The delivery head has isolation means to isolate a selected target area from its surroundings by substantially preventing escape of laser radiation, and viewing means are provided to enable an operator to view the selected target area. The apparatus is specifically for application in curing restorative or prophylactic tooth coatings, such as vitreous dental compositions or sol gels.

18 Claims, 3 Drawing Sheets

APPARATUS AND METHOD FOR DELIVERING LASER RADIATION TO A SUBSTRATE

INTRODUCTION

The invention relates to laser treatment of substrates, and more specifically to an apparatus and method for delivering laser radiation to a substrate. In particular it concerns an apparatus and a method of producing cosmetic or prophylactic coatings for teeth utilising such an apparatus.

BACKGROUND OF THE INVENTION

In attempting to prevent or reduce the incidence of tooth decay, and to inhibit decay after it has commenced, a number of compounds for forming highly durable coatings or fillings for teeth, and methods of using such compounds, have been considered in the past. Protective/cosmetic coatings and restorative surfaces for teeth must be highly durable and cosmetically acceptable.

In co-pending application WO-93/00878 a suitable vitreous dental coating composition is described, specifically a sol gel, xerogel or heat-consolidated gel composition, comprising a hydrolysable silicic ester, 1–4 moles water per mole of silicon, a solvent and a filler. In a typical use of such a composition the surface of the tooth is first prepared by cleaning, then the composition is applied to the tooth surface in a thickness of a few microns, and then the composition is cured or consolidated by heat treatment. This heat treatment stage is carried out by application of appropriate radiation energy. For this latter stage, it is important to safely deliver the correct amount of energy to the correct location in a sufficiently short time, preferably below or close to the thermal relaxation time of the tooth tissue, that is, within a few microseconds.

A suitable source of radiation energy for processing thin film of the type discussed above is a $CO_2$ laser producing pulsed or continuous wave laser light tuned to 10.6 µm, since such laser light is strongly absorbed by the natural tooth. Other laser radiation sources, such as Nd:YAG or argon lasers, with wavelengths in the near infra-red and visible ranges, can also be used.

The process described above has been successfully tested on extracted human teeth, but there are particular requirements associated with delivering the laser energy effectively and safely to a tooth in situ in a patient's mouth.

Patent document U.S. Pat. No. 4,445,858 teaches an apparatus for use in curing dental restorative materials by means of visible or ultraviolet light, incorporating a hand-held light wand whose end is spaced from the material to be cured by a conical shield. The device is not designed to be suitable for use in delivering laser radiation.

German patent application DE-A-3232007 describes a handpiece which is intended for dental treatment by laser, employing a laser beam transmitting glass fibre. The delivery end of the handpiece features a laser ejection cylinder provided with four circumferentially spaced cutaway portions to provide exhaust ports for an air supply through the laser delivery system.

Lasers have been increasingly used in the medical arena with ever improving clinical results for a number of years now. The controllable, intense light beams can be used for example to cut or vaporise tissue in many aspects of specialised surgery. However, in the dental treatment process presently of interest, different problems arise due to the specific safety considerations. An effective delivery system must be capable of being accurately controlled whilst ensuring that the risks inherent in the use of lasers are reduced as far as possible.

SUMMARY OF THE INVENTION

According to the invention, an apparatus is provided for delivering laser radiation to a substrate, said apparatus comprising:

a laser radiation source;

delivery means to transmit the laser radiation from the source; and a delivery head to direct the laser radiation from the delivery means onto the substrate, having isolation means to isolate a selected target area from its surroundings by essentially preventing escape of laser radiation, characterised in that viewing means non-transmissive of the laser radiation are provided to enable an operator to view the selected target area when the latter is isolated from its surroundings.

The provision of suitable viewing means is important because, when the target is isolated by the delivery head of the device, viewing access for the operator would otherwise become obstructed or severely restricted. Provision of the viewing means obviates this difficulty and the operator can effectively monitor the operation of the system in use.

The laser radiation source preferably comprises a $CO_2$ pulsed or continuous wave laser.

The laser radiation may be delivered by way of an articulated arm provided with laser light guiding means, such as a system of mirror elements or fibre optic means.

Preferably, the delivery head comprises focusing means and at least one optical scanner deflector, to control the delivery of laser radiation to the substrate.

To effectively fulfil the isolating function, the delivery head preferably has a body part, the isolation means comprising a shield defined by a socket projecting from the body part and having means for selectively sealing around the target area. Alternatively, the delivery head may have a tubular body, the isolation means comprising an extension piece with an end wall, the extension piece fitting onto the tubular body in sliding engagement therewith.

A number of different viewing means may be provided according to the present invention. At least one section of the delivery head may be transparent to visible light, or an optical eyepiece can be incorporated in the delivery head. Alternatively, or additionally, video monitoring means may be provided.

Additional features of the invention will be found in the more specific description and the drawings which follow.

BRIEF DESCRIPTION OF THE DRAWINGS

Embodiments of the invention will now be described, solely by way of example, with reference to the accompanying drawings, in which.

SPECIFIC DESCRIPTION OF THE INVENTION

Figure 1:
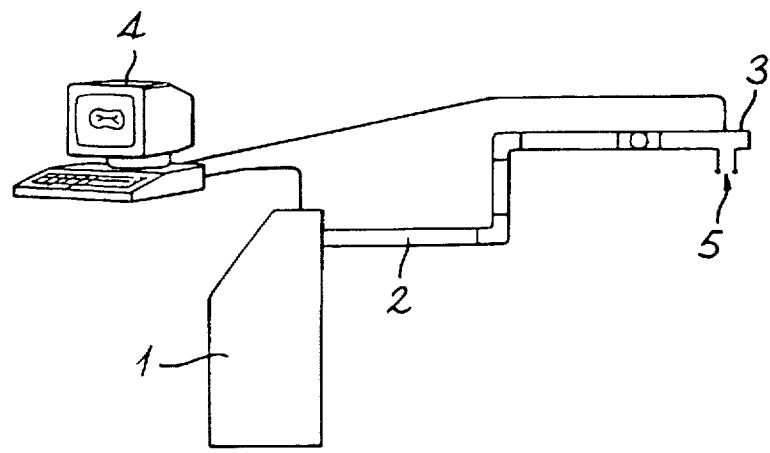
FIG. 1 shows the main components of a laser radiation delivery apparatus according to the invention.

FIG. 1 shows a laser energy delivery apparatus used to supply laser light to a tooth coating to be treated and comprising a laser light source 1, an articulated arm 2, a laser light delivery head 3 at the end of the articulated arm, and a control system 4. The arrangement of the delivery head 3 on the articulated arm 2 is similar to that of a standard dental handpiece.

Laser Light Source

The laser light source 1 contains a sealed, RF-excited $CO_2$ laser producing pulsed or continuous wave laser light at a wavelength of 10.6 μm. Other wavelengths and types of laser source are possible, such as a Nd:YAG laser (1.064 μm—near infra-red), an Er:YAG laser (2.94 μm—mid infra-red), an Ho:YAG laser (2.1 μm—mid infra-red), a CO laser (5 μm—mid infra-red), or a far infra-red $CO_2$ laser (9.6 μm). Alternatively a tunable $CO_2$ laser may be used to take advantage of the energy absorption of different wavelengths in the case of different materials. For laser wavelengths in the near infra-red and visible ranges, energy absorption can be enhanced by the inclusion in the tooth coating material of chromophores, such as transition metal ions.

Beam Delivery

The articulated arm 2 acts as a laser light transmission tube, and in a known manner has reflective mirrors suitably mounted at the various joints to accurately direct a laser beam to the delivery head 3, whilst allowing the arm to be manoeuvred into different positions to access a target. The beam may also be directed via fibre optic means, and although infra-red fibre optics appropriate for $CO_2$ laser wavelengths are not at present fully practicable (such wavelengths not being efficiently transmitted by standard silica-based fibres or hollow ceramic or metal waveguides), this transmission method is certainly suitable for other categories of laser light, such as that from the Nd:YAG laser.

The delivery head 3 receives the laser beam and delivers it to the surface to be treated via an opening 5.

A control system 4 is used by an operator to control the functioning of the apparatus, and is therefore connected to the laser source 1, to select the duration and various other criteria for the operation of the laser beam, and to the delivery head 3 to control the scanning operation described below. The control system 4 is also provided with means for entering details such as patients' names and means for monitoring various aspects of the operation of the system. The system is microprocessor-controlled and includes a VDU screen as part of the monitoring means.

Delivery Head

Figure 2:
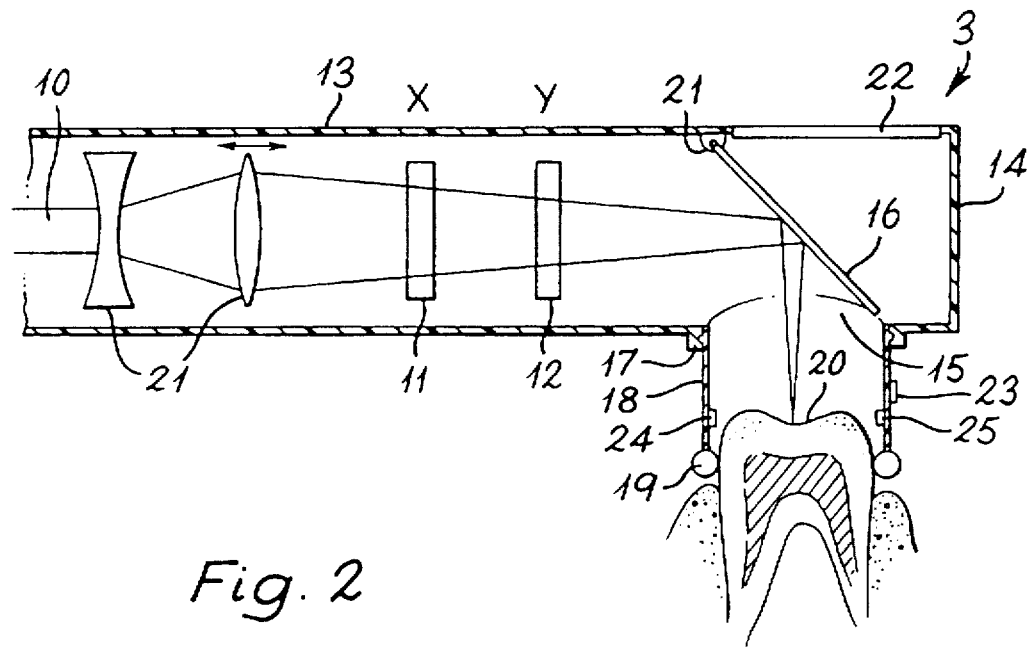
FIG. 2 diagrammatically illustrates one embodiment of the delivery head of the apparatus of FIG. 1 used to direct laser light onto the surface of a tooth.

FIG. 2 shows the delivery head 3 receiving the beam of laser light, indicated by reference numeral 10. Because of lack of uniformity of energy of a $CO_2$ laser beam over its entire cross section, it is not practical to irradiate the whole of an extended target area simultaneously, with different parts of the target area exposed to different parts of the beam cross section. For that reason the beam is focused to a small spot (10–500 μm in diameter, preferably between 50 and 100 μm) by means of lenses 21, which are movable so as to focus the beam at the appropriate point, thereby effectively eliminating hot spots across the beam cross section and producing instead a single point heat source which can be scanned across the target area using optical scanner deflectors, operating in directions transverse to one another and controlled by way of control system 4. The combination of small spot size and controlled scanning makes uniform heat treatment of the target area possible, which is necessary for producing a consistent, flawless glassy surface. The optical scanner deflectors may be galvanometer-based optical scanners (GBOSs), which are commonly used in applications which call for accurate positioning of a laser beam. As illustrated diagrammatically in FIG. 2, they may alternatively be solid-state acousto-optical crystal devices 11 and 12, in which the optical properties of a suitable crystal (e.g. $TeO_2$ or $LiNbO_3$) are locally varied by a strong acoustic wave generated at radio frequencies, so as to deflect a beam of light. Acousto-optical devices of this kind are more compact than GBOSs.

The beam focusing lenses and scanners are contained within a tubular housing 13 which is closed off by an end wall 14 and which features a side aperture 15 through which the beam can be directed by means of an angled mirror 16 mounted on a pivot 21 within the tubular housing as shown in FIG. 2. Typically, the tubular housing 13 may be cylindrical, about 16 cm in length, with a diameter of 1.8 cm for the portion destined to be inserted into the patient∝s mouth.

The aperture is fitted with a joint 17 for coupling to a socket 18 which serves as a shield to isolate a tooth from its surroundings. The purpose of this shield is to minimize the possibility of laser radiation escaping to the surroundings during operation of the laser curing apparatus. The laser radiation used is potentially harmful and the isolation means provides protection for other parts of the patients' mouth, such as soft tissue and other teeth, and also provides protection for the dentist or operator. In the embodiment illustrated in FIG. 2 the socket 18 is of short, flexible, approximately tubular form of a plastics material, one end being adapted to be attached to joint 17 and provided at the other end with an elastic O-ring 19 of a flexible material, to at least partially seal the tooth with the socket. The O-ring 19 may be inflatable to provide an air-tight seal, and alternatively or additionally the diameter of the socket may be adjustable to improve sealing. The delivery head 3 can be manoeuvred to fit the socket 18 over the occlusal surface of a molar or premolar tooth 20 to aid in location and to stabilise the apparatus on the target and to prevent, or at least greatly reduce, the possibility of laser light reaching any other part of the patient's mouth. The socket 18 also ensures that the delivery head is maintained at an optimum distance from the tooth surface. The socket 18 is readily detachable and can be discarded and replaced after use to prevent the possibility of contamination from one patient to another. According to the invention, the delivery head or its socket 18 is equipped with viewing means. For example, the socket may be transparent to visible light, or may feature a viewing port transparent to visible light, to assist in alignment of the delivery head and to enable an operator to view a selected target area on the tooth. In the case of a $CO_2$ laser such a transparent portion may be manufactured of glass or plastics material such as perspex, to be highly absorbent of radiation at that wavelength and thereby prevent escape of laser radiation.

Alternatively, an eyepiece (not shown) may be incorporated as a lateral attachment to the tubular housing 13 to enable the operator to view the target area. This may be a rotating, angled tubular eyepiece for ease of use. A beam splitter or similar is included within the delivery head to deflect to the eyepiece a portion of the light reflected through the optical system from the target. The eyepiece is designed to prevent transmission of radiation at the wavelength of laser light used for the curing process.

The delivery head 3 shown in FIG. 2 is also provided with light detector means 22 and may also feature a sensor 23 and/or opto-electronic means 24, 25, which will be described further below.

Figure 3:
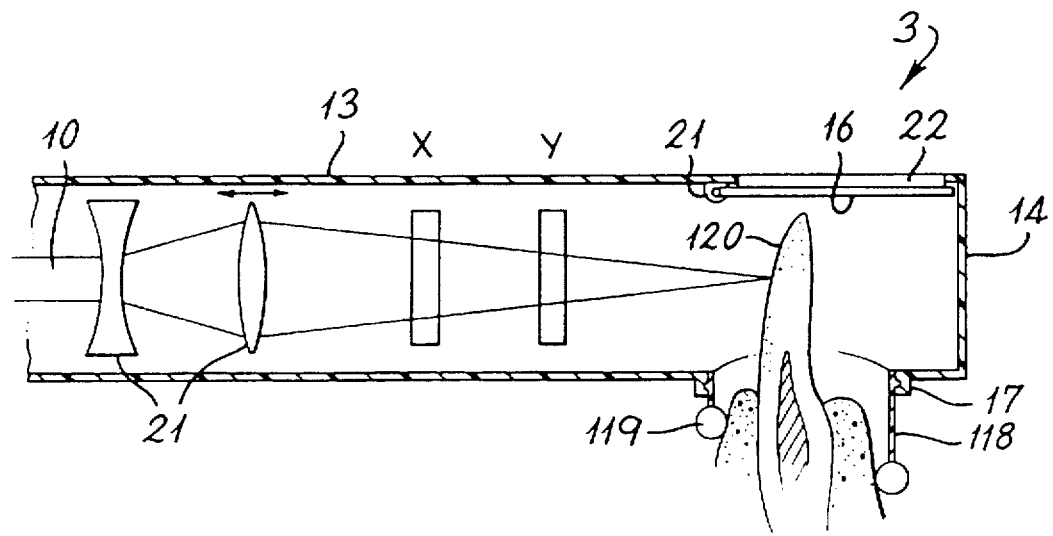
FIG. 3 shows an adapted version of the delivery head of FIG. 2.

In FIG. 3 the same delivery head is shown but in this case it is being used to cosmetically or prophylactically treat the visible surface 120 of an incisor, where the coating is applied to the front surface of the tooth. An appropriately shaped alternative socket 118, with O-ring seal 119, is fitted to joint 17 so as to provide a continuation of end wall 14, thereby reducing the danger of any laser light which travels past the tooth causing damage to any part of the subject's mouth. It is to be noted that mirror 16 is not required in this case and can be folded away as shown by means of hinge 21.

Clearly other interchangeable disposable sockets may be used with the delivery head, selected to suit different teeth in different patients.

Figure 4:
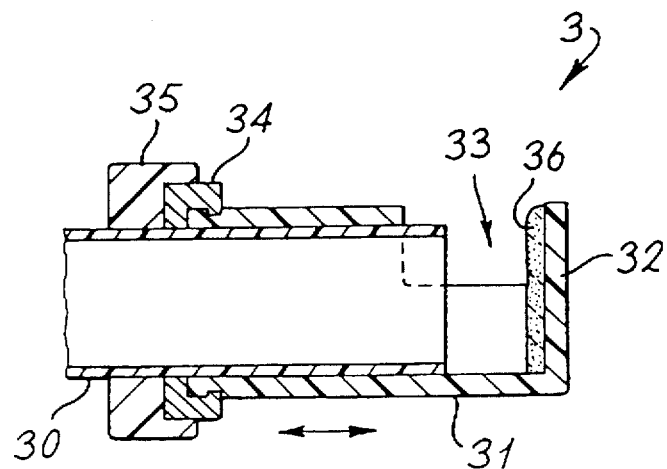
FIG. 4 shows another embodiment of the delivery head.

FIG. 4 illustrates a section of an alternative delivery head, also to be used in treating the visible surface of an incisor, which features adjustment means to accommodate in an alternative manner the particular size of tooth to be treated and thus shield the tooth effectively. The delivery head comprises an open cylindrical tube 30 on which a closely fitting tubular endpiece 31 can be fitted, the endpiece being closed by end wall 32 and having a side aperture 33 to receive the tooth. The tubular endpiece is engaged by a clamping ring 34 and rotating locking ring 35. On the inner side of endwall 32 rubber impression material 36 is mounted. The endpiece 31 can be telescoped along the tube 30 as indicated by the arrow to provide an opening that closely fits the size of the tooth. The clamping means can then be operated to lock the two parts in position relative to one another, thus fixing the size of opening for the duration of the treatment process. Tubular endpiece 31 may be of glass or another suitable transparent material.

Focusing Means

As explained above, to ensure the beam parameters at the tooth surface are appropriate for curing a sol-gel derived coating which has been applied to the tooth surface, it is required to focus the laser beam relative to the surface to produce a spot with the required diameter. Since this spot is to be scanned over the—probably irregular—surface of the tooth, it may be necessary to instantaneously control the focusing during the scanning operation. If a relatively long focal length is selected then the process will be less sensitive to the exact position of the tooth surface, but some means of focus control will still be required.

It is also desirable that the scanning system should be correctly aligned prior to beginning the curing process, and to this end visible laser radiation is directed along the same projected path of the $CO_2$ laser beam. An He-Ne (Helium-Neon) laser with a wavelength of 633 µm, which is also contained in the source 1, is used for this purpose, providing an 'aiming beam' of visible light which is arranged, by means of a combining beam splitter (not shown), such that the aiming beam follows the same path as the curing radiation. Further reference to this arrangement is made below under the heading 'Scanning System'.

Within the delivery head 3 or the source 1 a light detector is arranged to receive light reflected from the irradiated surface. In FIG. 2, for example, a sensor device of an automatic focusing unit, or another photoelectrical detection element 22 is mounted behind the mirror 16, which for this purpose is a partially reflecting mirror, such that visible light reflected from the tooth surface passing through the partially reflecting mirror is detected by the element 22. The light detector element can be used to provide a signal which is sent to the control system 4 and which can be used to indicate the presence of the tooth surface and to calculate its distance from the light detector, this information being used to control the focusing of the $CO_2$ laser beam during the subsequent curing stage.

Safety Measures

It is highly desirable from the point of view of safety that the curing laser radiation is not delivered until the delivery head is correctly positioned, for example until the socket 18 in FIG. 2 is correctly located over the tooth to fully isolate it from the rest of the patient's mouth, particularly from the surrounding soft tissues.

This may be accomplished by means of the reflected He-Ne visible light detected by the light detector 22. This supplies a 'proximity signal', and thereby fulfils a safety function to prevent the curing laser operating unless the tooth surface is within a certain range. Alternatively, mechanical means, such as a spring-loaded mechanical contact, may be provided in association with the socket itself to determine whether it is appropriately located. A sensor such as a strain gauge 23 may be provided on the flexible socket 18 to detect deformation in the socket due to contact with the tooth, or a pressure sensor may be built into the coupling joint 17. Either sensor can furnish a signal to prevent or allow the firing of the curing laser. As a further alternative, an opto-electronic system may be used to detect the presence or absence of a tooth. An LED 24 and a photo sensor 25 may be provided on opposite sides of the inside of the socket 18, a safety signal being provided only if the path of light between the LED and the photosensor is broken by the presence of a tooth.

During use of the system, there is a danger of small amounts of vapour and debris produced by the heat treatment process entering the delivery head and reaching the optical and mechanical components within. A positive pressure is therefore preferably provided within the delivery head to reduce this risk. Additionally an aspiration system may be provided in or adjacent to the socket to remove vapours produced during the curing process. Moreover, a stream of forced air may be provided in or adjacent to the socket to assist in drying of the tooth surface during the curing operation.

Scanning System

Figure 5:
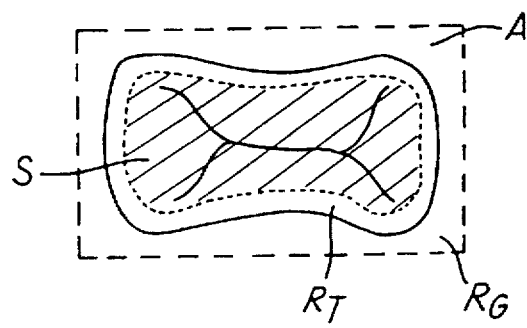
FIG. 5 diagrammatically illustrates the process of scanning the surface of a tooth with the apparatus of the invention.

The He-Ne laser already described may be used to select the target area to be scanned. For this purpose, the reflected light from the He-Ne laser can be monitored by appropriate detection means and the precise area to be scanned at the curing stage can be automatically determined, thus ensuring that a sufficient area of the tooth surface is irradiated whilst minimising the danger that the laser may be directed at an area beyond the edges of the tooth surface to be treated, such as the patient's gum tissue. FIG. 5 illustrates this technique. The intensity of reflected light from the tooth surface is considerably greater than that from the surrounding light-absorbing gum tissue, and the distribution of reflected light intensity will therefore give an indication of the size and shape of the tooth surface. If the He-Ne beam is scanned across an area A (larger than the area of the tooth surface) the intensity of the reflected signal can be compared with a threshold value. If the reflected light is above this value then tooth surface is present ($R_T$) and if the reflected light is below this value then gum tissue is present ($R_G$). The control system 4 is set up to record the reflected light value $R_T$ or $R_G$ as a function of the instantaneous position of the scanning light spot, and this gives the shape and size of the tooth surface. This may then be de-magnified automatically to define a reduced area, shown in FIG. 5 as shaded area S within the dotted line, which is then scanned by the gel-curing laser beam. A scanning field smaller than the entire tooth surface is selected as, for safety reasons, it may not be desirable that the whole surface, right out to its very periphery, should be scanned by this more powerful laser beam.

As an alternative, once the tooth shape has been determined, the operator may select a predetermined shape from a repertoire of geometrical shapes stored by the control system 4, as being suitable for the tooth in question and fitting within the boundaries of the tooth as determined by the He-Ne scan. This shape may then be used to determine the actual area which is irradiated by the $CO_2$ laser.

With this system the operator is able to view the tooth, by means of a viewing means including a display generated by means of the He-Ne scan. Alternatively charged-coupled devices (CCDs) can be built into the delivery head to provide means of visual inspection of the tooth and the proposed target area before the curing is carried out. Using the control system 4 the operator can select the area to be scanned and the scanning pattern to be used, either by freehand control or by the techniques discussed above.

Identification of Consolidation

It is desirable that the operator is able to check whether the coating has been fully cured by the laser treatment. A detector may be provided in the delivery head to monitor the surface emissivity from the tooth, this giving a measure of the temperature attained at the surface and hence an indication of the degree of consolidation. For this purpose an infra-red diode, or an array of such diodes, may be mounted in the head to measure the temperature or the distribution of temperature across the target zone. For adequate curing of sol-gel derived coatings a temperature of 200° C.–800° C. is needed in a total curing period of the order of 0.1 s.

Alternatively a photodetection system may be used to examine the cured coating. If fluorescent chromophores (such as fluorescein) are added to the gel these will thermally decompose during the heat treatment. The tooth surface can then be interrogated by means of a light beam, for example, the He-Ne laser beam, and the fluorescence measured, giving an indication of the presence of cured coating and of the degree and uniformity of consolidation.

Operation

In operation of the system, the delivery head is fitted with an appropriate socket, and the apparatus is manoeuvred to position the socket over the selected tooth after the tooth has been cleaned and the coating gel has been applied to the surface to be treated. This isolates the tooth, and hence the selected target area, from its surroundings. The tooth is then scanned with the He-Ne laser light and the size and shape of the target area is determined. Preferably, the operator selects the target area while viewing the tooth by any of the means already described. The operator then starts the aspiration means and the positive pressure means for the delivery head, if required, and the curing operation can then be initiated, the $CO_2$ laser beam only being activated when the system has detected a safety signal from the proximity signal or otherwise. The laser beam spot is then scanned across the selected target zone in a zig-zag, raster or other pattern, selected as required and to avoid hotspots, to deliver the correct amount of energy in the appropriate time to consolidate the gel coating to its glassy state. The target zone may be scanned a number of times, first at low power (less than 5 w) to drive off solvents, then at a higher power (around 10 w) to fully effect the curing. An appropriate high frequency tone can be used to indicate when the $CO_2$ beam is engaged. The degree and uniformity of consolidation can then be checked as described above, and any non-uniformity is corrected by further irradiation.

Figure 6:
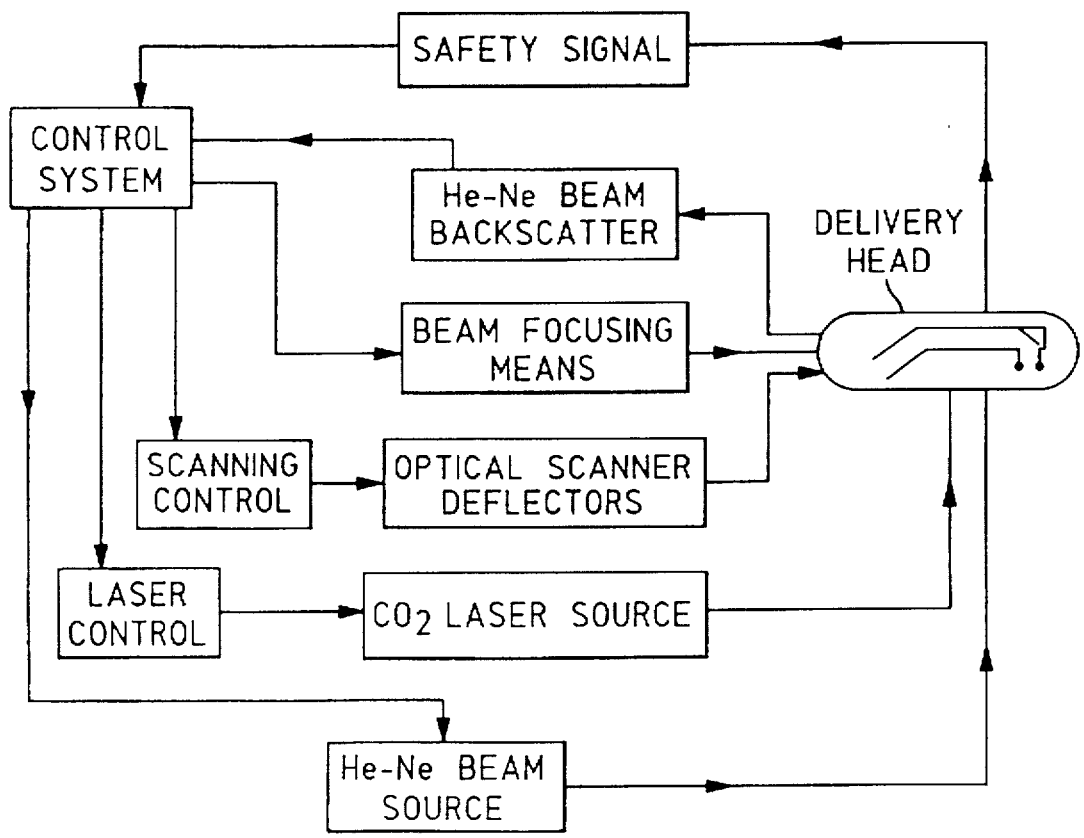
FIG. 6 is a block diagram representing the various operational components of the apparatus, and the connections therebetween.

The block diagram of FIG. 6 shows the various operational components and how they are interconnected.

As an alternative to the small spot scanning system described above, a TEA-$CO_2$ laser may be used. This is capable of producing a beam with uniform energy distribution across the area of the beam, and therefore the beam can simply be directed to a selected target area and switched on for the desired time. The delivery of the beam would not therefore require focusing means, the irradiated area being up to, say, 1 cm in diameter. Masking could be used to protect surrounding areas and prevent their being irradiated.

I claim:

1. Apparatus for delivering laser radiation to a substrate, said apparatus comprising:

a laser radiation source;

delivery means for transmitting the laser radiation from the source;

a delivery head including a housing for directing the laser radiation from the delivery means onto the substrate;

aperture means provided in said housing for receiving said substrate;

isolation means associated with said aperture means for isolating a selected target area by essentially preventing escape of laser radiation to a surrounding area; and viewing means non-transmissive to the laser radiation for enabling an operator to view the selected target area when said selected target area is isolated from its surroundings.

2. Apparatus according to claim 1, in which the laser radiation source comprises a $CO_2$ pulsed or continuous wave laser.

3. Apparatus according to claim 1, in which the delivery means comprises an articulated arm provided with laser light guiding means.

4. Apparatus according to claim 1, in which the delivery head comprises focusing means and at least one optical scanner deflector.

5. Apparatus according to claim 1, in which said housing is comprised of a tubular body and the isolation means comprises a sliding extension piece with an end wall, the extension piece fitting onto the tubular body in sliding engagement therewith.

6. Apparatus according to claim 1 in which the viewing means comprises at least one section of the delivery head transparent to visible light.

7. Apparatus according to claim 1, in which the viewing means comprises a video monitor.

8. Apparatus according to claim 1 in which the delivery head is provided with a means for indicating proximity of the substrate.

9. Apparatus according to claim 1 in which gas transfer means is provided in connection with the delivery head for aspirating the delivery head and/or providing a positive gas pressure thereto.

10. Apparatus according to claim 1 in which a safety device is associated with the delivery head to prevent operation of the laser with no a received signal indicating correct positioning of the delivery head with respect to the substrate.

11. Apparatus according to claim 1, for use in heat treatment of a curable composition applied to a tooth surface including means for identifying a degree of consolidation of the composition.

12. Apparatus according to claim 1 in combination with a control system to control and monitor operation of the apparatus.

13. A method for delivering laser radiation to a substrate to which a curable composition has been applied, comprising use of an apparatus of claim 1.

14. Apparatus according to claim 1, including a He-Ne laser radiation source for use in focusing and/or monitoring of the laser radiation.

15. Apparatus according to claim 14 in which the He-Ne laser includes means to provide a visual display of the substrate target area.

16. Apparatus according to claim 1, in which the delivery head has a body part and the isolation means comprises a shield defined by a socket projecting from the body part, having means for selectively sealing the socket around the target area.

17. Apparatus according to claim 16 in which the sealing means is inflatable and capable of providing a substantially air-tight seal.

18. Apparatus according to claim 16, in which the socket is detachably connected to the delivery head.

* * * * *